(12) United States Patent
Gokaraju et al.

(10) Patent No.: US 6,875,891 B2
(45) Date of Patent: Apr. 5, 2005

(54) PROCESS FOR PREPARING HIGHLY WATER SOLUBLE DOUBLE SALTS OF HYDROXYCITRIC ACID PARTICULARLY ALKALI AND ALKALINE EARTH METAL DOUBLE SALTS

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Sridhar Pratha, Andhra Pradesh (IN)

(73) Assignee: Laila Impex, Andhra Pradesh (IN)

( * ) Notice: Subject to any disclaimer, the term of this patent is extended or adjusted under 35 U.S.C. 154(b) by 0 days.

(21) Appl. No.: 10/803,986

(22) Filed: Mar. 19, 2004

(65) Prior Publication Data

US 2004/0229953 A1 Nov. 18, 2004

(30) Foreign Application Priority Data

May 12, 2003 (IN) .................................... 402/MAS/2003

(51) Int. Cl.$^7$ ............................................ C07C 59/265
(52) U.S. Cl. ...................................... 562/584; 514/574
(58) Field of Search .......................... 562/584; 514/574

(56) References Cited

U.S. PATENT DOCUMENTS 6,160,172 A * 12/2000 Balasubramanyam et al. ... 562/584
6,395,296 B1 * 5/2002 Balasubramanyam et al. ... 424/439

FOREIGN PATENT DOCUMENTS

WO    WO 00/48983    *  8/2000

* cited by examiner

*Primary Examiner*—Rita Desai
*Assistant Examiner*—Hector M. Reyes
(74) *Attorney, Agent, or Firm*—Rader, Fishman & Grauer PLLC

(57) ABSTRACT

This invention relates to a novel process for preparing highly water soluble alkaline earth metal and alkali metal double salts of hydroxycitric acid. These salts are practically odourless and has negligible taste and are therefor useful as nutraceuticals. Aqueous extract of the fruits belonging to *Garcinia* species are treated to precipitate its alkaline earth metal salts such as the calcium salt. This sparingly soluble product is dissolved in alkali hydroxide and the pH of the solution is adjusted by adding purified extract of the fruit rind. Ca/Na or Ca/K double salts are particularly useful.

12 Claims, No Drawings

PROCESS FOR PREPARING HIGHLY WATER SOLUBLE DOUBLE SALTS OF HYDROXYCITRIC ACID PARTICULARLY ALKALI AND ALKALINE EARTH METAL DOUBLE SALTS

This invention relates to a process for preparing highly water soluble double salts of hydroxycitric acid particularly alkali and alkaline earth metal double salts.

Fruits, particularly the rind of fruits, of the plant belonging to *Garcinia* species are a rich naturally occuring source of hydroxycitric acid. *Garcinia* species grow abundantly in India and in the south East Asian countries. 'Kokum' an extract of *Garcinia* fruits is used in imparting tart flavour to dishes, particularly meat and fish dishes. Ayurveda, the traditional herbal medicinal system, considers *Garcinia* as one of the herbs that is beneficial to heart. *Garcinia* or malabar tamarind has also received considerable attention in recent times as a nutraceutical for effective obesity control.

Hydroxycitric acid has been known to be beneficial for the control and reduction of mammalian body weight. In particular, the (−) hydroxycitric acid isomer and derivatives thereof are found to inhibit fatty acid and cholesterol synthesis. These compounds also function as a natural anorectic agent in mammals. This particular stereoisomer of hydroxycitric acid occurs in the free acid form and in the lactone form. However, only the free acid form of (−) hydroxycitric acid is found to exhibit bio-activity.

Naturally occuring hydroxycitric acid and its derivatives may be obtained by known methods of extraction of the fruits of the species *Garcinia*. One such method has been disclosed by Lewis Y. S., Methods in enzymology (J. M. Lowenstein, Ed, vol.13, p.613, Academic Press N.Y. 1969).

Certain physical properties of hydroxycitric acid and its derivatives are not ideally suited for their use as nutraceuticals. For instance, hydroxycitric acid exhibits very strong sour taste while its calcium salt though not very pungent in taste is poorly soluble in water thereby reducing its bio-availability; the tripotassium salt of this acid is highly hygroscopic and is alkaline in nature. These undesirable characteristics such as taste and solubility affect the bio-availability or biological use of these compounds. It has been found that the double salt of Ca/K or Ca/Na of (−)—hydroxycitric acid are ideal for biological use, particularly, because of their ideal physical characteristics. Further, desirable properties of these double salts are their low sodium content in Ca/K double salt and balanced pH.

These double salts are highly water soluble, have no strong or undesirable taste and are practically odourless. These salts are therefore ideal for a variety of applications including beverages. Preparation of these double salts are disclosed in PCT WO 0015051 published on 23 Mar. 2000 having priority in U.S. patent application Ser No. 892,414 filed on 14 Jul. 1997; U.S. Pat. No. 6,160,172 dated 12 Dec. 2000 and U.S. Pat. No. 6,395,296 dated 28 May 2002.

The processes of preparing the double salt disclosed in the prior art are tedius and the final product obtained may contain harmful contaminants, thus limiting its utility value. For instance, the procedure disclosed in PCT WO 0015051 consists of converting calcium salt of (−)—HCA into free HCA and the free (−) HCA is partially neutralized by the addition of Ca (OH)$_2$ followed by complete neutralization with KOH. Removal of calcium phosphate and unreacted phosphoric acid from the reaction mixture is a cumbersome procedure. Indian patent no.182487 involves conversion of the calcium salt of (−) HCA into free HCA with oxalic acid. The liberated HCA is treated with sodium hydroxide followed by partial replacement of sodium by calcium by treating with calcium chloride. Removal of calcium oxalate and excess oxalic acid from the reaction mixture limits the utility of this method. U.S. Pat. No. 5,656,314 discloses conversion of calcium salt of hydroxycitric acid and into free acid with sulphuric acid. Purification of the final product obtained by this process also involves tedious procedure.

Thus, the object of this invention is to convert calcium salt of hydroxycitric acid into a highly water soluble calcium, potassium or calcium, sodium double salt using a simple cost effective process. Inorganic or organic acids are not used in this process of conversion consequently, removal of undesired by-products and excess acid from the reaction mixture is avoided. Surprisingly, it is observed that the Ca/K double salt is largely free of the lactone form of hydroxycitric acid and when dissolved in water, the salt does not equilibrate between the free form and the lactone form. Further, desirable properties of the Ca/K double salt is its balanced pH and a low (<1%) sodium content.

Fruits of *Garcinia atrovindis, Garcina cambogia* or *Garcinia indica* are extracted with water, preferably at room temperature. The rind of the fruits are preferred for extraction as it contains a very high percentage of HCA. The aqueous extract is treated with calcium hydroxide to precipitate sparingly soluble calcium salt of hydroxycitric acid. The precipitated calcium salt is dissolved by adding aqueous potassium hydroxide. The desired calcium potassium double salt is obtained from this solution by adjusting its pH with purified aqueous extract of *Garcinia* rind.

Purified *Garcina* fruit rind extract may be obtained by treating the aqueous extract of the fruit rind with acetone, filtering the said treated extract to separate suspended solids therefrom and concentrating the filtrate which is used to adjust the pH of the alkaline solution in the process of preparing the double salts of HCA.

Calcium salt of HCA may also be prepared by neutralizing the aqueous extract of the fruits with sodium hydroxide followed by treatment with calcium chloride.

This invention relates to a process for preparing highly water soluble alkali metal/alkaline earth metal double salt of hydroxycitric acid which comprises the steps of precipitating sparingly soluble alkaline earth metal salt of hydroxycitric acid from an aqueous extract of the plants belonging to *Garcinia* species, dissolving said alkaline earth metal salt in aqueous alkali, adjusting the pH of said alkaline solution by adding an extract of *Garcinia* fruit thereto, purifying and drying the same thereafter to obtain highly water soluble double salts of hydroxycitric acid.

*Garcinia* fruits and fruit rinds are particularly preferred because of their high hydroxycitric acid content. The description herein is limited to the preparation of Ca/K or Ca/Na double salts, though the same procedure is applicable for the preparation of any alkali metal/alkaline earth metal double salts. The first step in the process is the preparation of calcium salt of hydroxycitric acid from the aqueous plant extract. This may be carried out by neutralization of the extract with an alkali. Calcium hydroxide and sodium hydroxide are preferred when calcium hydroxide is added to the aqueous plant extract, sparingly soluble calcium salt of hydroxycitric acid gets precipitated. However, if sodium hydroxide is used for neutralization, calcium chloride must be added for converting the sodium salt to the calcium salt. This precipitate is washed, with water and the resulting calcium salt is converted into the double salt by dissolving the same in aqueous potassium or sodium hydroxide followed by adjustment of its pH by adding purified *Garcinia* fruit extract thereto.

The following examples are particularly described the preferred embodiment of this invention.

EXAMPLE I

Step 1: Preparation of Calcium Salt of HCA

About 12.5 kg of aqueous extract of *Garcinia* fruit containing about 9% of total solids was treated with 400 g of Ca(OH)$_2$ at room temperature. The resulting precipitate of calcium salt of HCA was filtered and dried in vacuum for about 4 hours. Product yield was about 560 g.

In another variation about 10 kg of *Garcinia* fruit extract containing about 9% of total solids was treated with 1.7 L of 20% NaOH solution under stirring for 2 hours. pH of this solution was adjusted to 7 by adding 200 ml of 50% HCl. Subsequently 4 L of 20% solution of calcium chloride was added to this to precipitate the calcium salt of HCA. This precipitate was filtered and washed with water and dried under vacuum at 80° C. for a period of 4 hours to yield 550 g of the salt.

Step 2: Conversion of Calcium Salt of HCA to Calcium Potassium Double Salt of HCA About 280 g of the calcium salt prepared by the step above was suspended in 2.8 L of water and about 2 L of 10% KOH solution was added to it under stirring. The pH of the resulting solution was adjusted to 8.0 by adding purified *Garcinia* fruit rind extract. The solution thus obtained was treated with 150 g of activated charcoal at about 80° C. for an hour and then filtered using celite as filter aid. The filtrate was then concentrated to a total solid content of 25% and spray dried to give calcium/potassium double salt of hydroxycitric acid. Yield is found to be about 580 g.

EXAMPLE II

Step 1: Calcium Salt of Hydroxycitric Acid was Prepared According to Example I.

Step 2: Conversion of Calcium Salt of HCA to Calcium Potassium Double Salt.

About 20 g of the calcium salt prepared above was suspended in 200 ml of water and the pH was adjusted to 13 by adding 10% solution of KOH under stirring. The pH of this solution was then adjusted to pH 8 by purified *Garcinia* fruit rind extract. The solution thus obtained was treated with activated charcoal (10 g) at 80° C. for one hour and then filtered. The filtrate was concentrated and then spray dried to yield 30 g of calcium potassium double salt.

EXAMPLE III

Step 1: Preparation of Calcium Salt of HCA was Carried Out as Per Example I.

Step 2: Conversion of Calcium Salt into Ca—Na Double Salt of HCA.

About 280 g the calcium salt obtained in step 1 was suspended in 2.8 L of water and about 1.4 L of 10% NaOH was added thereto under stirring. The pH of the resulting solution was adjusted to 8 by adding purified *Garcinia* fruit rind extract. The solution was treated with 150 g of activated charcoal at 80° C. for an hour and then filtered. The filtrate was concentrated and spray dried to give calcium sodium double salt of hydroxycitric acid. Approximate yield 540 g.

In all the above examples the purified *Garcinia* extract used is obtained by treating an aqueous extract of the fruit rind with acetone. Settled mass from the extract has been filtered off and the filtrate has been used for adjusting the pH.

This invention also includes calcium potassium or calcium sodium double salts of hydroxycitric acid.

What is claimed is:

1. A process for preparing highly water soluble alkaline earth and alkali metal double salts of hydroxycitric acid comprising the steps of precipitating sparingly soluble alkaline earth metal salts of hydroxycitric acid from an aqueous extract of the plants belonging to *Garcinia* species, dissolving said alkaline earth metal salts in aqueous alkali, adjusting the pH of said alkaline solution by adding an extract of purified *Garcinia* fruit extract thereto, purifying and drying the same thereafter to obtain highly soluble double salts of hydroxycitric acid.

2. The process as claimed in claim 1, wherein calcium salt of hydroxycitric acid is precipitated from the aqueous extract of *Garcinia* plant by adding calcium hydroxide thereto.

3. The process as claimed in claim 1, wherein calcium salt of hydroxycitric acid is precipitated from the aqueous extract of *Garcinia* plant by adding a solution of sodium hydroxide thereto followed by adding a solution of calcium chloride.

4. The process as claimed in claim 1, wherein the *Garcinia* plant is *Garcinia atroviridis*, *Garcinia cambogia* or *Garcinia indica*.

5. The process as claimed in claim 1, wherein the fruit rind of *Garcinia* species is subjected to aqueous extraction.

6. The process as claimed in claim 2, wherein said calcium salt is treated with KOH solution having a concentration of 5 to 50%, weight/volume.

7. The process as claimed in claim 1, wherein said purified *Garcinia* fruit extract is obtained by treating the aqueous extract thereof with acetone, and separating the insolubles therefrom.

8. The process as claimed in claim 1, wherein said aqueous extract containing the double salt is purified by treatment with activated charcoal, filtered and then spray dried.

9. The process as claimed in claim 8, wherein the filtrate is concentrated and dried under vacuum.

10. The process as claimed in claim 3, wherein said calcium salt is treated with KOH solution having a concentration of 5 to 50% weight/volume.

11. The process as claimed in claim 10, wherein said calcium salt is treated with KOH solution having a concentration of 5 to 15% weight/volume.

12. The process as claimed in claim 6, wherein said calcium salt is treated with KOH solution having a concentration of 5 to 15% weight/volume.

* * * * *